United States Patent
Hölzer et al.

(10) Patent No.: US 11,904,056 B2
(45) Date of Patent: Feb. 20, 2024

(54) CAPSULE SHELL COMPRISING A CORE-SHELL POLYMER AND A CELLULOSE

(71) Applicant: Evonik Operations GmbH, Essen (DE)

(72) Inventors: Bettina Hölzer, Bensheim (DE); Manfred Aßmus, Bickenbach (DE); Kathrin Nollenberger, Darmstadt (DE)

(73) Assignee: Evonik Operations GmbH, Essen (DE)

( * ) Notice: Subject to any disclaimer, the term of this patent is extended or adjusted under 35 U.S.C. 154(b) by 235 days.

(21) Appl. No.: 17/438,886

(22) PCT Filed: Mar. 5, 2020

(86) PCT No.: PCT/EP2020/055848
§ 371 (c)(1),
(2) Date: Sep. 13, 2021

(87) PCT Pub. No.: WO2020/182611
PCT Pub. Date: Sep. 17, 2020

(65) Prior Publication Data
US 2022/0142929 A1    May 12, 2022

(30) Foreign Application Priority Data
Mar. 14, 2019 (EP) .................... 19162778

(51) Int. Cl.
*A61K 9/48* (2006.01)
*A61J 3/07* (2006.01)
*B29C 41/14* (2006.01)
*B29K 33/00* (2006.01)
*B29K 105/00* (2006.01)

(52) U.S. Cl.
CPC ............. *A61K 9/4816* (2013.01); *A61J 3/077* (2013.01); *B29C 41/14* (2013.01); *B29K 2033/12* (2013.01); *B29K 2105/0064* (2013.01); *B29K 2105/0094* (2013.01)

(58) Field of Classification Search
CPC ........ A61K 9/4816; A61J 3/077; B29C 41/14; B29K 2033/12; B29K 2105/0064; B29K 2105/0094
See application file for complete search history.

(56) References Cited

U.S. PATENT DOCUMENTS

| | | | |
|---|---|---|---|
| 4,138,013 A | 2/1979 | Okajima | |
| 9,107,451 B2 * | 8/2015 | Skalsky | A61K 9/4891 |
| 9,775,814 B2 | 10/2017 | Teles et al. | |
| 9,844,511 B2 | 12/2017 | Nollenberger et al. | |
| 11,523,992 B2 * | 12/2022 | Jain | A61K 9/4816 |
| 2009/0041666 A1 * | 2/2009 | Goldstein | A61K 31/05 |
| | | | 424/9.1 |
| 2010/0113620 A1 | 5/2010 | Perrie et al. | |
| 2014/0086997 A1 | 3/2014 | Nollenberger et al. | |
| 2015/0010620 A1 | 1/2015 | Benameur et al. | |
| 2015/0132372 A1 | 5/2015 | Benameur et al. | |
| 2015/0366815 A1 * | 12/2015 | Teles | A61K 9/4825 |
| | | | 514/769 |
| 2021/0361585 A1 | 11/2021 | Guha et al. | |

FOREIGN PATENT DOCUMENTS

| | | | | |
|---|---|---|---|---|
| EP | 0714656 A1 * | 2/2001 | ........... | A61K 9/4816 |
| WO | 2011/012369 | 2/2011 | | |
| WO | WO-2012171575 A1 * | 12/2012 | ............ | A61K 47/30 |
| WO | 2014/018279 | 1/2014 | | |
| WO | 2019/096833 | 5/2019 | | |
| WO | 2012/171575 | 12/2021 | | |

OTHER PUBLICATIONS

International Search Report issued in PCT/EP2020/055848 dated Apr. 7, 2020.
Written Opinion issued in PCT/EP2020/055848 dated Apr. 7, 2020.
European Search Report issued in EP 19 16 2778 dated Sep. 17, 2019.
Nathalie Huyghebaert et al. "Alternative method for enteric coating of HPMC Capsules resulting in ready-to-use enteric-coated capsules." *European Journal of Pharmaceutical Sciences*, 21 (2004) 617-623.
Rajeswari Kola et al. "A detailed description of synthetic and natural polymers which are used in the formulation of sustained release drug delivery system: a review," *Journal of Chemical and Pharmaceutical Sciences*, Jul.-Sep. 2013, vol. 6, Issue 3, pp. 161-169.
Anonymous, "Evonik launches EUDRAGIT FL 30 D-55, an advanced combination polymer that sets a new benchmark for enteric coatings," Oct. 4, 2018, pp. 1-2, retrieved from https://corporate.evonik.com/media/pressattachments/c458/n76768/a37397.pdf on Sep. 16, 2019.
Evonik Industries, "Guidelines for Formulation Development and Process Technology for Enteric Coatings," Mar. 1, 2009, pp. 1-3, retrieved from http://www.pharma-polymers.com/NR/rdonlyres/1EA56E7C-0D38-4084-8DF9-53F9B484FD5D/0/31 eGuidelinesforFormulationDevelopmentandProcessTechnologyforEntericCoatings.pdf.
U.S. Office Action dated Apr. 20, 2022 in U.S. Appl. No. 17/595,145, 11 pages.

(Continued)

*Primary Examiner* — Blessing M Fubara
(74) *Attorney, Agent, or Firm* — Grüneberg and Myers PLLC

(57) ABSTRACT

A capsule shell contains 40 to 99% by weight of a core-shell polymer and 1 to 60% by weight of a cellulose. The core-shell polymer contains 50 to 90% by weight of a core, containing polymerized units of 65 to 75% by weight of ethyl acrylate and 25 to 35% by weight of methyl methacrylate; and 10 to 50% by weight of a shell, containing polymerized units of 45 to 55% by weight of ethyl acrylate and 45 to 55% by weight of methacrylic acid.

16 Claims, No Drawings

(56) References Cited

OTHER PUBLICATIONS

U.S. Appl. No. 17/595,145, filed Nov. 10, 2021, Jain et al.
U.S. Pat. No. 9,844,511, Dec. 19, 2017, 2014/0086997, Nollenberger et al.
U.S. Office Action dated Jun. 14, 2022, in U.S. Appl. No. 15/733,083, 12 pages.
U.S. Appl. No. 15/733,083, filed May 13, 2020, 2021/0361585, Guha et al.

* cited by examiner

CAPSULE SHELL COMPRISING A CORE-SHELL POLYMER AND A CELLULOSE

CROSS-REFERENCE TO RELATED APPLICATIONS

This application is the National Stage entry under § 371 of International Application No. PCT/EP2020/055848, filed on Mar. 5, 2020, and which claims the benefit of priority to European Application No. 19162778.5, filed on Mar. 14, 2019. The content of each of these applications is hereby incorporated by reference in its entirety.

FIELD OF THE INVENTION

The invention is concerned with a capsule shell, comprising a core-shell polymer, which may be a copolymer derived from a two-stage emulsion polymerization process, and a cellulose.

BACKGROUND OF THE INVENTION

U.S. Pat. No. 4,138,013 describes hard shell capsules with enteric properties. The hard shell capsules comprise telescopically engaged body and cap portions. The capsule body and cap portions are formed by dip-molding using a homogeneous film-forming mixture selected (1) hydroxypropyl methyl cellulose and an ammonium salt of cellulose acetate phthalate or (2) gelatin and an ammonium salt of a copolymer of (meth)acrylic acid and (meth)acrylic acid alkyl ester. The capsules themselves have already enteric properties without applying a further enteric coating layer.

US2010/0113620A1 describes enteric pharmaceutical capsules. The capsule is consisting of (a) a film-forming water-insoluble polymer, such as HPMC (b) an acid-insoluble polymer, such as alginate, (c) a gelatinizing agent, such as gellan gum (d) an auxiliary for gelation, such as sodium or potassium ions, (e) at least one plasticizer and (f) optionally coloring or flavoring agents.

WO2011/012369A2 describes a coating agent for the dip coating of capsule halves. The coating composition for the enteric coating of capsule halves is made from a water-soluble or water-swellable polymer material in a dipping process, in the form of an aqueous dispersion or solution, comprising a mixture of (meth)acrylate copolymers with enteric or neutral properties.

WO2012/171575A1 describes a coating composition suitable for pharmaceutical applications. The coating composition comprises core-shell polymers derived from two-stage emulsion polymerization processes.

EUDRAGIT® FL 30 D-55 (Evonik Nutrition & Care GmbH, Darmstadt, Germany) is a commercially available 30% by weight aqueous dispersion of a copolymer from a two-stage emulsion polymerization process, with a core of about 75% by weight, comprising polymerized units of 70% by weight of ethyl acrylate and 30% by weight of methyl methacrylate, and a shell of about 25% by weight, comprising polymerized units of 50% by weight ethyl acrylate and 50% by weight methacrylic acid.

WO2014/018279A1 describes a film composition for hard shell capsules. A film disintegration test using a ball sample holder according to European Pharmacopeia (seventh edition, 2011, Disintegration of tablets and capsules) is described.

US2015/0010620A1 describes bulk enteric capsule shells, comprising cellulose acetate phthalate (CAP) and a processing aid selected from polyoxyethylene-polyoxypropylene-polyoxyethylene tri-block polymers. Disclosed are also dip-moulding processes for the manufacture of bulk enteric hard capsule shells.

US2015/0132372A1 describes aqueous dispersions of controlled release polymers and shells and capsules thereof.

Hard shell capsules are well known as containers for pharmaceutical or nutraceutical active ingredients. Hard shell capsules for pharmaceutical or nutraceutical purposes are assembled from two matching shells, the cap and the body, which are telescopically joined. Most capsule shells for hard shell capsules, capsule caps and capsule bodies, are industrially produced by dipping pin molds (moulding pins) into an aqueous-based film-forming composition and subsequently withdrawing the pins from the composition. The film formed on the surface of molding pins is dried, stripped off the pins and is cut to a desired length. Most hard shell capsules respectively the shell from that they are assembled, are usually made form gelatin or HPMC. Both capsule types disintegrate in the environment of gastric juices in the stomach.

SUMMARY OF THE INVENTION

Hard shell capsules, made from capsule shells, are widely used as containers for biologically active ingredients of oral pharmaceutical or nutraceutical dosage forms. Many biologically active ingredients are sensitive to acidic conditions or shall not be set free in the stomach but in the intestine. Thus, there is a need for capsules that are resistant against acidic conditions of the stomach but disintegrate at the higher pH conditions in the intestine.

The coating of filled and closed hard shell capsules made from gelatin or HPMC with enteric polymers is possible but requires an additional and often difficult to perform coating step. Often additional bandings have to be applied to ensure the tightness of the coated capsules. The pre-coating of capsule shells with enteric polymers is another attempt, which however often causes problems with unstable capsule shell dimensions. Thus, the manufacture of entire capsule shells from enteric polymer based materials could be an alternative to the drawbacks of the coating technology.

Common enteric polymers may confer enteric protection and dissolve at higher pH only when applied in thin coating layers, for instance in the range of 10 to 50 µm. However, the walls of capsule shells have to be much thicker, around 80 to 250 µm, in order to assure the dimension stability of the capsule. The problem is that when such capsule shells are made of an enteric polymer material, the capsules will not disintegrate at the higher pH of the intestine for many hours because of the thickness of the wall material.

Many or probably most of the worldwide produced capsule shells are manufactured by the so-called dip-coating technology. Steel pins are dipped into aqueous dispersions of the wall material for the capsule shell and are subsequently removed to let the attached wet wall material be dried on the pins. The capsule shells are then removed from the pins and cut to desired length. The problem is that the aqueous dispersions for the wall material of the capsule shells must meet a certain viscosity to attach to the pins without dropping during the process.

Most attempts to use (meth)acrylate copolymers as capsule shell materials, especially copolymers of methacrylic acid and methyl methacrylate or copolymers of methacrylic acid and ethyl acrylate, have failed so far. Thus, there is a need to provide capsule shells made from pure synthetic enteric capsule materials.

In order to overcome the drawbacks of the background art, the invention as disclosed offers a capsule shell comprising 40 to 99% by weight of a core-shell polymer, comprising 50 to 90, preferably 70 to 80% by weight of a core, comprising polymerized units of 65 to 75% by weight of ethyl acrylate and 25 to 35% by weight of methyl methacrylate, and 10 to 50, preferably 20 to 30% by weight of a shell, comprising polymerized units of 45 to 55% by weight of ethyl acrylate and 45 to 55% by weight of methacrylic acid, and 1 to 60% by weight of a cellulose.

The invention allows to provide capsule shells for hard shell capsules with a wide range of different disintegration profiles.

DETAILED DESCRIPTION OF THE INVENTION

Hard Shell Capsules and Capsule Shells

Hard shell capsules for pharmaceutical or nutraceutical purposes are well known to a skilled person. A hard shell capsule is a two-piece encapsulation capsule comprising of two capsule shells, called the capsule body and the capsule cap. A capsule shell in the sense of the invention is therefore a capsule body or a capsule cap. The capsule body and cap material is usually made from a hard and sometimes brittle polymeric material. A hard shell capsule comprises a body and a cap. Body and cap are usually of a one end open cylindrical form with a closed rounded hemispherical form on the opposite end. The shape and size of the cap and body are matching such that the body can be pushed telescopically with its open end into the open end of the cap, resulting in a tightly closed hard shell capsule.

A capsule shell in the sense of the invention is therefore a capsule body or a capsule cap. A hard shell capsule comprises two matching capsule shells, which are the capsule body and the capsule cap. A biologically active ingredient, which may be a pharmaceutical active ingredient or a nutraceutical active ingredient, may be filled into the capsule body. The capsule body may then be closed by adding the capsule cap, resulting in a closed hard shell capsule according to the invention. The disintegration of the hard shell capsule respectively the release of the active ingredient is dependent on the polymeric composition of the capsule shell material, especially on the ratio between the core-shell polymer and the cellulose as described. A wide spectrum of different release profiles from slightly delayed release over enteric USP-conform release and strongly delayed release may be realized depending on the desired use.

The capsule body and the capsule cap usually comprise a potential overlapping matching area (overlap area) outside the capsule body and inside the capsule cap, which partially overlaps when the capsule is closed in the pre-locked state and totally overlap in the final-locked state. When the capsule cap is partially slid over the overlapping matching area of the capsule body, the capsule is in the pre-locked state. When the capsule cap is totally slid over the overlapping matching area of the capsule body, the capsule is in the final-locked state.

The maintenance of the pre-locked state or of the final-locked state is usually supported by snap-in locking mechanisms of the capsule body and the capsule cap such as matching encircling notches or dimples, preferably elongated dimples. Usually dimples are preferred for fixing the body and the cap in the pre-locked state. As a non-binding rule, the matching area of dimples is smaller than the matching area of encircling notches. Thus, snapped-in dimples may be snapped-out again by applying less forces than those that would be necessary to snap-out a snapped-in fixation by matching encircling notches.

Hard shell capsules are commercially available in different sizes. Hard shell capsules are usually delivered as empty containers with the capsule body and capsule cap already positioned in the pre-locked state and on demand as separate capsules halves, bodies and caps. Pre-locked hard shell capsules may be provided to a capsule-filling machine, which performs the opening, filling and closing of the capsule into the final-locked state. Usually hard shell capsules are filled with dry materials, for instance with powders or granules comprising a biologically active ingredient, which may be an active pharmaceutical ingredient or an active nutraceutical ingredient.

Core-Shell Polymer

The capsule shell as disclosed is comprising a mixture of 40 to 99% by weight of a core-shell polymer and 1 to 60% by weight of a cellulose.

The core-shell polymer is comprising 50 to 90, preferably 70 to 80% by weight of a core, comprising polymerized units of 65 to 75% by weight of ethyl acrylate and 25 to 35% by weight of methyl methacrylate, and 10 to 50, preferably 20 to 30% by weight of a shell, comprising polymerized units of 45 to 55% by weight of ethyl acrylate and 45 to 55% by weight of methacrylic acid.

A suitable core-shell polymer is EUDRAGIT® FL 30 D-55 (Evonik Nutrition & Care GmbH, Darmstadt, Germany), which is a commercially available 30% by weight aqueous dispersion of a copolymer from a two-stage emulsion polymerization process, with a core of about 75% by weight, comprising polymerized units of 70% by weight of ethyl acrylate and 30% by weight of methyl methacrylate, and a shell of about 25% by weight, comprising polymerized units of 50% by weight of ethyl acrylate and 50% by weight of methacrylic acid.

Suitable core-shell polymers that are usually derived from two-stage emulsion polymerization processes and their synthesis are well-known for instance from WO2012/171575A1.

Pharmaceutically or Nutraceutically Acceptable Excipients

Optionally up to 50% by weight of pharmaceutically or nutraceutically acceptable excipients such as pigments, coloring agents or separating agents, such as Mg stearate, talc or glycerol monostearate, may be added. However, usually less than 25, preferably less than 10% by weight or no excipients at all are added. The core-shell polymer, the cellulose and, if present, the optional excipients may add up to 100%. Pharmaceutically or nutraceutically acceptable excipients, are excipients well known to the skilled person in pharmacy, galenics or nutrition technology, are classified as harmless to the human or animal health and allowed to be used in pharmaceutical or nutraceutical compositions.

Cellulose

The capsule shell, which can be either a capsule cap or a capsule body, comprises 1 to 60% by weight of a cellulose.

Preferably, the capsule shell is comprising 40 to 99% by weight of the core-shell polymer, and 1 to 60% by weight of a cellulose, wherein the cellulose shows a viscosity when measured as a 2% by weight aqueous dispersion at 20° C. with a Brookfield viscometer, spindle 1, in the range of about 1 to 3, preferably of about 1.5 to 2.5 mPa*s.

The capsule shell may also comprise 95 to 99% by weight of the core-shell polymer, and 1 to 5% by weight of a cellulose, wherein the cellulose shows a viscosity when measured as a 2% by weight aqueous dispersion at 20° C.

with a Brookfield viscometer, spindle 1, in the range of about more than 3 and up to 6, preferably of about 4 to 5.5 mPa*s.

Preferably, the capsule shell is comprising 40 to 99% by weight of the core-shell polymer, and 1 to 60% by weight of a cellulose, wherein the cellulose shows a viscosity when measured as a 2% by weight aqueous dispersion at 20° C. with a Brookfield viscometer, spindle 1, of 1 to 3, preferably of 1.5 to 2.5 mPa*s.

The capsule shell may also comprise 95 to 99% by weight of the core-shell polymer, and 1 to 5% by weight of a cellulose, wherein the cellulose shows a viscosity when measured as a 2% by weight aqueous dispersion at 20° C. with a Brookfield viscometer, spindle 1, of more than 3 and up to 6, preferably of 4 to 5.5 mPa*s.

The cellulose may be a water-soluble cellulose, preferably a water-soluble cellulose of low viscosity, most preferred a hydroxypropyl methyl cellulose. A suitable, commercially available cellulose is for instance METHOCEL™ Premium VLV.

A low viscosity cellulose may be defined as a cellulose which shows a viscosity, when measured as a 2% by weight aqueous dispersion at 20° C. with a Brookfield viscometer, spindle 1, in the range of 1 to 6, preferably from 1.5 to 5.5 mPa*s.

Aqueous Dispersion

Disclosed is also an aqueous dispersion comprising water and 10 to 40% by weight of a composition comprising 40 to 99% by weight of a core-shell polymer, comprising 50 to 90% by weight of a core, comprising polymerized units of 65 to 75% by weight of ethyl acrylate and 25 to 35% by weight of methyl methacrylate, and 10 to 50% by weight of a shell, comprising polymerized units of 45 to 55% by weight of ethyl acrylate and 45 to 55% by weight of methacrylic acid, and 1 to 60% by weight of a cellulose.

Preferably, the aqueous dispersion shows a viscosity, measured with a Brookfield viscometer, spindle 1, at 20° C. in the range of 25 to 3,000, preferably 150 to 2,800 mPa*s.

Dimension of Capsule Shells/Capsules

The capsule shell as disclosed may have a thickness of the capsule shell wall of from about 80 to 250, preferably from about 100 to 220 μm. The capsule shell as disclosed may have a thickness of the capsule shell wall of from 80 to 250, preferably from 100 to 220 μm.

A capsule shell as disclosed may be a capsule body or a capsule cap. Usually, the capsule body is longer than the capsule cap. The outside overlapping area of the capsule body can be covered by the capsule cap in order to dose or to lock the capsule. In the closed state the capsule cap covers the outside overlap area of the capsule body either in a pre-locked state or in a final-locked state. In the final-locked state, the capsule cap covers the outside overlap area of the capsule body in total, in the pre-locked state, the capsule cap overlaps the outside overlapping area of the capsule body only partially. The capsule cap can be slid over the capsule body to be fixed in usually one of two different positions in which the capsule is closed either in a pre-locked state or in a final-locked state.

Within the context of the invention, a dosed capsule may show a total length in the range from about 5 to 50 mm. The diameter of the capsule cap (upper part) may be in the range from about 4 to 12 mm. The diameter of the capsule body (lower part) may be in the range from about 2 up to 10 mm. The length of the capsule cap may be in the range from about 4 to 20 mm and that of the capsule body in the range from 8 to 30 mm. The fill volume may be between about 0.1 and 2 ml.

Capsules may be divided, for example, into standardized sizes from 000 to 5.

A closed capsule of size 000 has, for example, a total length of about 28 mm, a diameter of the upper part of about 9.9 mm and a diameter of the lower part of about 9.5 mm. The length of the upper part is about 14 mm, that of the lower part of about 22 mm. The fill volume is about 1.4 ml.

A closed capsule of size 5 has, for example, a total length of about 10 mm, a diameter of the upper part of about 4.8 mm and a diameter of the lower part of about 4.6 mm. The length of the upper part is about 5.6 mm, that of the lower part of about 9.4 mm. The fill volume is about 0.13 ml.

Hard Shell Capsule

A hard shell capsule comprises two matching capsule shells, the capsule body and the capsule cap (or simply addressed as body and cap). The term "matching" shall mean that the capsule body and the capsule cap have dimensions that allow (usually after filling), that the capsule cap can be slid over the capsule body, usually in a locked position, to result in a tightly closed hard shell capsule. A closed hard shell capsule may contain a filling comprising a biologically active ingredient, which may be an active pharmaceutical ingredient or an active nutraceutical ingredient.

Dissolution Behavior

The dissolution or disruption behavior of a filled and closed capsule may be simulated by a rather simple "steel ball fall test". The rather simple test correlates well with more elaborate dissolution tests with filled and closed capsules. For this purpose, films of about 100 μm thickness are prepared from the different aqueous dispersions. The films of about 100 μm thickness are comparable to a typical capsule wall thickness. Each film may then be horizontally and tightly fixed between two plastic rings (inner diameter about 1.9 cm), separating the space between the two plastic rings. A pH 1.2 medium or a pH 6.8 buffer respectively (each according to USP, for instance USP 31) is filled into the void volume formed by the wall of the upper plastic ring and with the film as bottom. A steel ball (diameter about 1.1 cm, weight about 5.4 g) is added to simulate mechanical stress in the stomach or in the intestine on the film. The time until the steel ball breaks through the film may then be measured (s. also for instance the film disintegration test as described in WO2014018279A1, p. 8-9, and as described in European Pharmacopoeia, seventh Edition, 2011, disintegration of Tablets and Capsules).

Films with a "steel ball break-through time" in pH 1.2 medium of 1 to 30 min allow the manufacture of capsule shells for hard shell capsules, which disintegrate in a mode from fast to slightly delayed.

Films with a "steel ball break-through time" in pH 1.2 medium of more than 1 hour and a disintegration time in pH 6.8 buffer of less than 45 min allow the manufacture of capsule shells for hard shell capsules, which disintegrate in a USP-conform mode for enteric protection.

Films with a "steel ball break-through time" in pH 1.2 medium more than 1 hour and a disintegration time at pH 6.8 buffer of more than 45 min or up to 3 to 5 hours allow the manufacture of capsule shells for enteric protected hard shell capsules, with a strongly delayed disintegration profile.

Process for Preparing a Capsule Shell

Disclosed is a process (dip-moulding process) for preparing a capsule shell by the steps
  a) providing the core-shell polymer in the form of an aqueous polymer dispersion A,
  b) providing the cellulose in the form of an aqueous polymer dispersion B, c) mixing the polymer dispersions A and B to a mixed aqueous polymer dispersion (optionally pharmaceutically or nutraceutically acceptable excipients may be added as described before),
d) dipping a moulding pin, that has the inner complementary form of the capsule shell at its end with this end into the mixed polymer dispersion,
e) withdrawing the moulding pin from the polymer dispersion and drying the polymer dispersion on the moulding pin to form a film, which has the form of the capsule shell,
f) removing the capsule shell from the moulding pin.

The aqueous dispersion A in step a) may comprise 25 to 35% by weight of the core-shell copolymer.

The mixed aqueous dispersion in step c) may comprise 15 to 40% by weight of the core-shell copolymer, the cellulose and optionally pharmaceutically or nutraceutically acceptable excipients.

The mixed polymer dispersion in step c) may show a viscosity, measured with a Brookfield viscometer, spindle 1, at 20° C. in the range of 25 to 3,000, preferably from 250 to 2,800 mPa*s.

Optionally, post-processing steps such as cutting the length or post-drying may be added as known by a skilled person in the art.

EXAMPLES

Polymers

EUDRAGIT® FL 30 D-55 (Evonik Nutrition & Care GmbH, Darmstadt, Germany) is a 30% by weight aqueous dispersion of a copolymer from a two-stage emulsion polymerization process, with a core of about 75% by weight, comprising polymerized units of 70% by weight of ethyl acrylate and 30% by weight of methyl methacrylate, and a shell of about 25% by weight, comprising polymerized units of 50% by weight of ethyl acrylate and 50% by weight of methacrylic acid.

The viscosity of EUDRAGIT® FL 30 D-55 that was measured in a 30% by weight aqueous dispersion at 20° C. with a Brookfield viscometer spindle 1 is approximately 10 mPa*s.

METHOCEL™ Premium VLV is a very low viscosity hydroxypropyl methyl cellulose.

The viscosity of METHOCEL™ Premium VLV was measured as a 2% by weight aqueous dispersion at 20° C. with a Brookfield viscometer, spindle 1, in the range of about 2 mPa*s.

METHOCEL™ Premium E5 is a low viscosity hydroxypropyl methyl cellulose.

The viscosity of METHOCEL™ Premium E5 was measured as a 2% by weight aqueous dispersion at 20° C. with a Brookfield viscometer, spindle 1, in the range of 5 mPa*s.

Preparation of the Cellulose Solution 800 g of water were heated up to 80° C. 200 g of METHOCEL™ Premium VLV were added slowly, while stirring with a blade agitator. The suspension was cooled down to 20° C. while continuously stirring. METHOCEL™ Premium VLV dissolves during the cooling phase and a very high viscose solution is formed.

The viscosity of the 20% METHOCEL™ Premium VLV solution was measured at 20° C. with a Brookfield viscometer, spindle 3, in the range of 10,000 mPa*s or more (10,000 to 12,000 mPa*s).

850 g of water were heated up to 80° C. 150 g of METHOCEL™ Premium E5 were added slowly, while stirring with a blade agitator. The suspension was cooled down to 20° C. while continuously stirring. METHOCEL™ Premium E5 dissolves during the cooling phase and a very high viscose solution is formed.

The viscosity of the 15% METHOCEL™ Premium E5 solution was measured at 20° C. with a Brookfield viscometer, spindle 3, in the range of 3,000 mPa*s or more (3,000 to 3,500 mPa*s).

Preparation of the Mixed Dispersions

With the help of a blade agitator, EUDRAGIT® FL 30 D-55 was mixed with the according amount of METHOCEL™ solution to form the following aqueous dispersions.

EUDRAGIT® FL 30 D-55/METHOCEL™ Premium E5 polymer ratios:

TABLE 1

| EUDRAGIT ® FL 30 D-55 polymer/ METHOCEL ™ Premium E5 (w/w) | Viscosity mPa*s |
|---|---|
| 90:10 | >10,000 |
| 98:2 | 500 |

Due to the viscosity the ratio 90:10 is not suitable to prepare a film or as dipping solution for capsule manufacturing.

EUDRAGIT® FL 30 D-55/METHOCEL™ Premium VLV polymer ratios:

TABLE 2

| EUDRAGIT ® FL 30 D-55 polymer/ METHOCEL ™ Premium VLV (w/w) | Viscosity mPa*s |
|---|---|
| 50:50 | 2500 |
| 70:30 | 1030 |
| 90:10 | 280 |
| 98:2 | 50 |

The viscosity of all ratios is suitable to prepare a film or as dipping solution for capsule manufacturing.

Preparation of the Films

With the help of a doctor blade, a Teflon® board was coated with the suitable dispersions and dried at room temperature. The thickness of the resulting films was approximately 100 μm.

Test Procedure/Steel Ball Fall Test

The resulting films were tested according to WO2014018279A1 and as described in European Pharmacopeia (Seventh Edition, 2011, disintegration of Tablets and Capsules). Therefore, the films were fixed between 2 tubs (1.9 cm inner diameter). A steel ball (diameter 1.1. cm, weight 5.4 g) was placed on top of the film and the corresponding media was charged into the upper tube. The break-through time of the steel ball was measured.

Results: The results are summarized in table 3

TABLE 3

Break-through times of 100 μm films in the steel ball fall test

| | pH 1.2 | pH 6.8 | Remark |
|---|---|---|---|
| EUDRAGIT FL 30 D-55 Polymer/ METHOCEL ™ Premium VLV (w/w) | | | |
| 50:50 | Ca. 1 min | Ca. 1 min | Fast disintegrating |
| 70:30 | Ca. 20 min | Ca. 2 min | Slightly delayed |

TABLE 3-continued

Break-through times of 100 μm films in the steel ball fall test

| | pH 1.2 | pH 6.8 | Remark |
|---|---|---|---|
| 80:20 | >17 h | Ca. 8 min | USP-conform enteric |
| 85:15 | >17 h | Ca. 20 min | |
| 90:10 | >17 h | Ca. 25 min | |
| 98:2 | >17 h | Ca. 3 h | Strongly delayed |
| EUDRAGIT FL 30 D-55 Polymer/ METHOCEL™ Premium E5 (w/w) | | | |
| 90:10 | n.a. | n.a. | Viscosity too high to manufacture a film |
| 98:2 | >17 h | Ca. 3 h | Strongly delayed |

The invention claimed is:

1. A capsule shell, comprising:
a mixture of:
   (a) 40 to 99% by weight of a core-shell polymer,
      wherein the core-shell polymer comprises 50 to 90% by weight of a core, comprising polymerized units of 65 to 75% by weight of ethyl acrylate and 25 to 35% by weight of methyl methacrylate, and
      wherein the core-shell polymer comprises 10 to 50% by weight of a shell, comprising polymerized units of 45 to 55% by weight of ethyl acrylate and 45 to 55% by weight of methacrylic acid, and
   (b) 1 to 60% by weight of a cellulose;
wherein an aqueous dispersion comprising
   water, and
   10-40% by weight of the mixture,
   shows a viscosity, measured with a Brookfield viscometer, spindle 1, at 20° C. in the range of 25 to 3,000 mPa*s.

2. The capsule shell according to claim 1, wherein the cellulose shows a viscosity when measured as a 2% by weight aqueous dispersion at 20° C. with a Brookfield viscometer, spindle 1, in the range of 1 to 3 mPa*s.

3. The capsule shell according to claim 1, comprising 95 to 99% by weight of the core-shell polymer, and 1 to 5% by weight of the cellulose, wherein the cellulose shows a viscosity when measured as a 2% by weight aqueous dispersion at 20° C. with a Brookfield viscometer, spindle 1, in the range of more than 3 and up to 6 mPa*s.

4. The capsule shell according to claim 1, wherein the cellulose is a hydroxypropyl methyl cellulose.

5. The capsule shell according to claim 1, wherein a thickness of a wall of the capsule shell is from about 80 to 250 μm.

6. The capsule shell according to claim 1, wherein the capsule shell is a capsule body or a capsule cap.

7. The capsule shell according to claim 1, wherein the core-shell polymer comprises 70 to 80% by weight of the core, and 20 to 30% by weight of the shell.

8. A hard shell capsule, comprising:
two matching capsule shells according to claim 1.

9. The hard shell capsule according to claim 8, wherein the hard shell capsule is closed and contains a filling comprising a biologically active ingredient.

10. A process for preparing a capsule shell according to claim 1, the process comprising:
   a) providing the core-shell polymer in the form of an aqueous polymer dispersion A,
   b) providing the cellulose in the form of an aqueous polymer dispersion B,
   c) mixing the polymer dispersion A and the polymer dispersion B into a mixed aqueous polymer dispersion,
   d) dipping a moulding pin, that has an inner complementary form of the capsule shell at its end, with this end into the mixed polymer dispersion,
   e) withdrawing the moulding pin from the mixed polymer dispersion and drying a polymer dispersion on the moulding pin to form a film, which has the form of the capsule shell, and
   f) removing the capsule shell from the moulding pin.

11. The process according to claim 10, wherein the aqueous polymer dispersion A in a) comprises 25 to 35% by weight of the core-shell polymer.

12. The process according to claim 10, wherein the mixed aqueous polymer dispersion comprises the aqueous polymer dispersions A and B at a ratio of A:B from 99:1 to 40:60.

13. The process for preparing a capsule shell according to claim 10, wherein the mixed aqueous polymer dispersion of step c) shows a viscosity, measured with a Brookfield viscometer, spindle 1, at 20° C. in the range of 25 to 3,000 mPa*s.

14. The capsule shell according to claim 1, wherein in the core-shell polymer, the core comprises polymerized units of 70% by weight of ethyl acrylate and 30% by weight of methyl methacrylate.

15. The capsule shell according to claim 1, wherein the cellulose is hydroxypropyl methyl cellulose and has a viscosity when measured as a 2% by weight aqueous dispersion at 20° C. with a Brookfield viscometer, spindle 1, in the range of about 1.5 to 2.5 mPa*s.

16. An aqueous dispersion, comprising:
   water, and
   10 to 40% by weight of a composition, and
   1 to 60% by weight of a cellulose,
   wherein the composition comprises 40 to 99% by weight of a core-shell polymer, comprising 50 to 90% by weight of a core, comprising polymerized units of 65 to 75% by weight of ethyl acrylate and 25 to 35% by weight of methyl methacrylate,
   wherein the core-shell polymer comprises 10 to 50% by weight of a shell, comprising polymerized units of 45 to 55% by weight of ethyl acrylate and 45 to 55% by weight of methacrylic acid, and wherein the aqueous dispersion shows a viscosity, measured with a Brookfield viscometer, spindle 1, at 20° C. in the range of 25 to 3,000 mPa*s.

* * * * *